United States Patent [19]
Taylor et al.

[11] Patent Number: 5,895,843
[45] Date of Patent: Apr. 20, 1999

[54] IN SITU SENSOR FOR CRITICAL CORROSION CONDITIONS IN A MATERIAL

[75] Inventors: S. Ray Taylor; Patrick A. Cella, both of Charlottesville, Va.

[73] Assignee: The University of Virginia Patent Foundation, Charlottesville, Va.

[21] Appl. No.: 08/856,982

[22] Filed: May 15, 1997

Related U.S. Application Data

[60] Provisional application No. 60/017,781, May 15, 1996.
[51] Int. Cl.⁶ .................................................. H01C 17/00
[52] U.S. Cl. ............................................ 73/86; 324/700
[58] Field of Search ..................................... 73/86; 324/700

[56] References Cited

U.S. PATENT DOCUMENTS

| | | |
|---|---|---|
| 4,217,544 | 8/1980 | Schmidt ............................. 73/86 |
| 4,703,253 | 10/1987 | Strommen ......................... 324/700 |
| 4,762,427 | 8/1988 | Hori et al. . | |

*Primary Examiner*—Robert Raevis
*Attorney, Agent, or Firm*—Oblon, Spivak, McClelland, Maier & Neustadt, P.C.

[57] ABSTRACT

An in situ sensor for monitoring the degree of corrosion of rebar in a concrete structure relies on a four-point resistance measure of a test wire embedded in the concrete structure. The resistance across the wire is compared with the resistance of a reference wire, which is corrosion resistant. As corrosion advances, the cross-sectional area of the wire decreases, effectively increasing the resistance measured. The sensor may be used to measure corrosion inhibitor performance, and the effect of dilution.

8 Claims, 2 Drawing Sheets

WIRES EMBEDDED AT MULTIPLE LEVELS IN CEMENTITIOUS MATERIAL TO OBSERVE DIFFUSIONAL PROCESSES.

RESISTANCE OF WIRE EMBEDDED IN 50% SLAG MORTAR
1/8 INCH BELOW THE PONDED SURFACE

RESISTANCE OF WIRE EMBEDDED IN PLAIN MORTAR
3/8 INCH BELOW THE PONDED SURFACE

IN SITU SENSOR FOR CRITICAL CORROSION CONDITIONS IN A MATERIAL

This application is a regular National application claiming priority from Provisional Application, U.S. application Ser. No. 60/017,781 filed May 15, 1996.

BACKGROUND OF THE INVENTION

1. Field of the Invention

This invention pertains to an in situ sensor for determining the degree and progress of corrosion of metal or alloy, for example steel, in a matrix structure. Methods of monitoring the progress of corrosion in such structures, as well as methods of determining the effectiveness of corrosion inhibitors and the effects on corrosion inhibitors of environmental dilution, are also disclosed.

2. Background of the Prior Art

The provision of a non-conductive matrix, defining a composition of matter, a structure, or a useful article, provided with conductive metal or alloy therein, is a common engineering composition. A wide variety of matrices are familiar to those of ordinary skill in the art. Among the most common matrices are concrete, refractory ceramics, polymeric coatings or masses (including reinforced resins, filled resins and foams) gels and vitrified glass like compositions. These compositions, and the articles and structures made therefrom, can all be described as being provided of a continuous matrix of the identified matrix material, with conductive elements incorporated in, typically embedded in, the matrix material. Thus, in concrete, steel reinforcement (rebar) is typically employed. Structures prepared from a polymeric matrix include high stiffness, high technology compositions such as aircraft and aerospace parts, which typically use reinforcing fibrous material such as carbon and graphite fibers, or fiberglass yarns, as well as lower strength filled resins, foams and the like. These may be provided with conductive elements for the purposes of reinforcement, to effect resistance heating, or to provide conductivity to the structure as a whole. Similarly, vitrified glass compositions may be provided with electrically conductive elements embedded therein, for example, to carry a current for the purpose of local heating, as in a windshield defroster, or as a reception antenna, for a radio and the like. Additionally, the matrix need not be solid. A wide variety of gels are employed across which a current may be desirably supplied. The most familiar of these matrices provided with metal or metal alloys is reinforced concrete, and this invention is discussed, in exemplary fashion, in terms of reinforced concrete. It will be apparent, however, that corrosion of steel or metal alloys embedded in a matrix is common to all of these structures. It is also common to metal or metal alloy structures that are embedded or coated with plastic film, such as underground storage tanks and the like.

In both concrete and high strength polymer matrixes, metal and metal alloys which are subject to corrosion are provided for reinforcement. The corrosion impacts the integrity and strength performance of the structure in question, and may reduce it below critical values.

The impact of reinforcing steel (rebar) corrosion on the performance life of concrete is now well recognized. For example, more than half of the bridges in the United States are affected by corrosion and approximately 20% have been deemed structurally deficient.

Rebar corrosion is of concern to manufacturers and users of concrete, rebar, and admixtures. This costly form of damage affects both building and highway construction, but there is no clear, reliable way to determine the rate of material loss of rebar embedded in concrete. Measuring the open circuit potential, for example, is easy and inexpensive but unreliable, producing errors three orders of magnitude and higher. Measuring linear polarization is complex, but is encumbered due to the potential drop in the concrete; electrochemical impedance spectroscopy can overcome that problem, but the results are extremely difficult to interpret and expensive to acquire.

One of the most important methods of mitigating rebar corrosion is through the addition of corrosion inhibitors into the concrete mix. Although such admixtures have been used commercially for years, there are no standard tests or specifications for their performance. Tests that are in use have serious shortcomings and do not fully exploit sophisticated electrochemical techniques.

To illustrate, the ASTM G-109 method (Wiss, Janey, Elstner Associates, Inc.) measures galvanic current between the top and bottom rebar mat during wet/dry cycling. Although galvanic polarization is a critical aspect of rebar corrosion, this test does not provide information on the total corrosion rate; it ignores the steady state corrosion current of the top-most layer, which could be significant. Moreover, corrosion in the mid-section of the bar may go undetected and misleading currents can be created by the elctroplater's tape required on the ends of the rebar. This test also cannot establish consistent galvanic couple from sample to sample and lacks statistical data and minimal criteria for inhibitor performance.

The search for a standard test is complicated by the diversity of inhibitors, which may be oxidizing or non-oxidizing anodic, cathodic, oxygen or chloride scavenging, film forming, and so on. Although manufacturers will naturally cite the test that makes their product stand out as a top performer, users require a more balanced approach for a realistic evaluation of all types of corrosion inhibiting admixtures.

There are also various electrochemical testing methods available: open circuit potential ($E_{oc}$), polarization resistance ($R_p$) via linear polarization and $R_p$ via electrochemical impedance spectroscopy (EIS). These methods must be used carefully, which is not the case in most reported studies. For example, real time correction (iR) for linear polarization is typically ignored, which causes underestimation of the corrosion rate. When the Stern Geary Equation and the anodic and cathodic Tafel slopes ($B_a$ and $b_c$) are used, the literature generally assumes some value, such as 26 or 46 mV, for all inhibitors. Finally, most tests wrongly assume that the corrosion current is uniform over the surface.

The testing methods themselves also have inherent advantages and disadvantages. Open circuit potential is easy and nondestructive, but can be ambiguous; it reveals the relative ratio of anodic to cathodic areas but provides no information on reaction kinetics. Linear polarization and EIS provide accurate reaction kinetics data but take several hours per $R_p$ determination and limit the size of the test matrix, since only 10 samples per day can be run. Additional time may be needed to resolve ambiguities in the distributed element response in EIS spectra or in the Tafel slope in linear polarization data.

Developing an accurate test to evaluate corrosion requires a thorough understanding of concrete material science, corrosion, electrochemical test methods, and inhibitor evaluation. Our sensor provides sensitive, unambiguous corrosion data at low cost, and can monitor changes in corrosion aggressiveness over time. This sensor is particularly suitable for monitoring the performance of corrosion inhibitors under various conditions and for gathering large data pools for statistical analysis and standardization.

Our probe is designed to be a standard which can be used by engineers, technicians and scientists to assess the efficacy of commercial corrosion inhibiting admixtures or matrix chemistries or diffusion rates of aggressive species or mitigating agents. Our test is simple and easy, many more samples can be evaluated for more accurate trend and statistical analysis.

SUMMARY OF THE INVENTION

The above objects, and others detailed below, are achieved by using a sensitive four-point resistance probe, embedded, in situ, in the matrix such as concrete or concrete structure to be monitored, so as to give a highly accurate resistance reading. Specifically, a metal or alloy wire, for example steel, is embedded in concrete or other matrix. As used herein, the term "wire" is intended to convey a continuous conductive member of small cross-section. This would include therein films, printed circuits, etc. If steel is used, it may be selected so as to carefully reflect conventional rebar, or rebar selected, in chemistry and microstructure. Four leads are attached to the wire (two leads establish current and two leads measure voltage) of established length. The wires are electrically connected to a highly sensitive measurement device, such as a conventional microohmmeter or constant current source in connection with a high resolution digital volt meter, to allow the detection of very slight changes in resistance. The changes in resistance are measured against the same values obtained for a reference wire, a wire which is corrosion resistant or shielded from the corrosive environment. In one embodiment, the wire is coated at one or both ends, so that leads attached with space confined to the coated area constitute the reference wire, whereas leads attached to portions across exposed wire provide the measurement value. In an alternative embodiment, separate leads are attached to an embedded wire and a reference wire embedded in the same matrix. The reference wire is shielded from corrosive agents in the matrix.

In either event, slight changes in resistance values (a loss in cross-sectional area of the wire due to corrosion increases resistance) allows monitoring and measurement of corrosion initiation and propagation, status of the concrete structure, measurement of the effectiveness of various corrosion inhibitors, as well as the effective diffusivity of aggressive and mitigating agents.

DETAILED DESCRIPTION OF THE INVENTION

As noted above, this invention is applicable to any article of manufacture in which a matrix, particularly but not exclusively solid matrices, is provided with metal or metal alloy components embedded therein. A wide variety of such compositions are employed in existing technology. In addition to reinforced concrete, there are a large number of resin matrices in which metal or metal alloy components are embedded. Examples include radomes, aerospace structural parts, coated steel underground storage tanks, piping and appurtenances. Additionally, refractory ceramics, vitrified materials of a variety of types, including resistance heating, and for reinforcement in particular directions, particularly, for example, for tempered materials are provided with metal or alloy embedded members. All of these matrix materials are susceptible to the inclusion of water, and the incorporation, migration into, and diffusion into the mass thereof, by corrosive species, which include chloride, sulphate and carbonate ions. Thus, each such matrix material, with metal or metal alloy materials embedded in the matrix, is subject to corrosion of the incorporated metal or metal alloy, and a drop in performance, or failure, based thereon. This invention is widely applicable to all these matrices, although described in detail, below, in terms of reinforced concrete. Because reinforced concrete structures are ubiquitous throughout the United States, and failures thereof present immediate health and security concerns, this embodiment is selected for illustration. The invention is not intended, and should not be understood, to be so limited.

Figure 1:
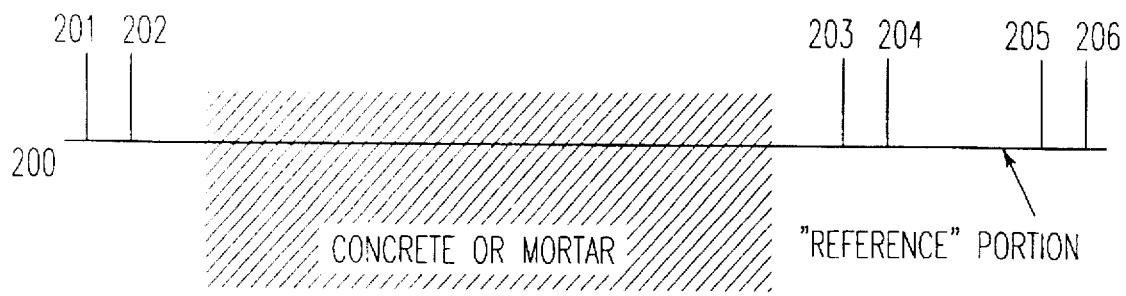
FIG. 1 is a schematic illustration of the sensor invention of this application, wherein a single wire constitutes both corrosion sensor wire and reference wire.

This invention embraces both the in situ sensor described above and below, and the methods of application of the same. The senor may be variously used to monitor the progress of corrosion in a concrete structure, and assess its structural integrity, to measure the effectiveness of various inhibitors in inhibiting or reducing the rate of corrosion, as well as the effects of local environment on the progress of corrosion. A typical sensor is illustrated in FIG. 1. In this figure, the probe wire 200 is embedded in concrete. The wire is coated at at least one end indicated at "Reference" portion. The probe is provided with six leads attached to the probe wire, leads 201–206, which are coated wires which carry to a four-point resistance measurement device. To measure the resistance of the embedded portion of wire 200, leads 201 and 204 are connected to a constant current source, and leads 202 and 203 are connected to a potential measurement instrument (ohmmeter). To measure the resistance of the Reference Portion, leads 203 and 206 are connected to the current source, and leads 204 and 205 to the instrument for measuring potential. The measurement device is preferably a conventional microohmmeter, or in the alternative, a constant current source in combination with a volt meter, for instance, a 6.5 digital volt meter. With the latter arrangement, a loss of one nanometer can be accurately detected, due to corrosion, if a 1 mm diameter reference wire is employed. Note that neither the current source nor the meter is illustrated.

Figure 2:
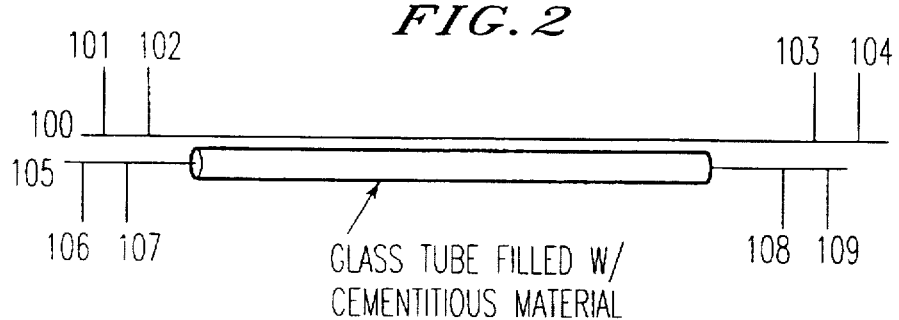
FIG. 2 illustrates an alternate embodiment of the invention, wherein the performance of an embedded wire is compared against the performance of a reference wire.

An alternate embodiment is illustrated in FIG. 2. In this case, embedded wire 100 has four leads, 101–104, for a four-point resistance measurement, while reference wire 105 similarly has four leads 106–109. Similarly to the probe of FIG. 1, to measure resistance of embedded wire 100, leads 101 and 104 are connected to a constant current source and leads 102 and 103 to a potential measurement instrument. The resistance of reference wire 105 is measured by connecting leads 106 and 109 to the current source and 107 and 108 to the meter. Reference wire 220 is prepared from a corrosion-resistant material or a material that is otherwise shielded from the concrete environment. Thus, in one embodiment, reference wire 220 is a polymeric coated wire. Alternatively, gold wire may be used. In a preferred embodiment, the reference wire is itself embedded in a glass tube filled with a cementitious material similar to that of the monitored structure, and placed in close proximity to the test wire. This allows identical starting conditions, but suppresses corrosion due to the exclusion of the environmental factors, such as chloride ions, which mediate corrosion.

Although the composition of rebar is not consistent, most rebar is prepared from 1040 steel. Wire of 1040 steel, or carbon steel wire close to rebar chemistry, is preferable selected. To mimic, as closely as possible, both rebar chemistry and microstructure, the reference wire and embedded wire are heat treated at about 800–1,200° F. for about one hour. This creates a similar oxide formation, and microstructure, to that exhibited by conventional rebar.

Figure 3:
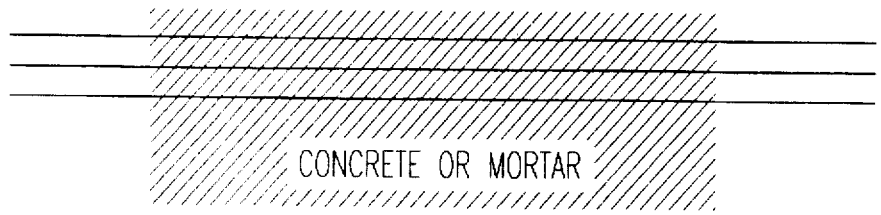
FIG. 3 illustrates, schematically, the use of a plurality of probes of the invention to monitor diffusion processes.

Advantageously, a large number of wires are located throughout the structure to be monitored, including some placed close to the exterior, and others placed more centrally in the interior of the concrete structure as illustrated in FIG. 3. This allows the creation of an overall picture of performance, and structural integrity, avoiding "spot influences" that do not reflect the overall state of corrosion in the structure. Placement should be determined taking into consideration both areal and depth coverage. At a single location, in two dimensions, probes may be placed at mutiple depths to monitor rates of penetration of either aggressive ($Cl^-$, $SO_4$, $CO_2$) or mitigating (topically applied inhibitor composition) agents.

As described in detail below, the same sensor can be used to evaluate potential corrosion inhibitors, as well as the effects of dilution (wash out).

Our simple, unambiguous electrically based test determines the initiation time and the corrosion rate of steel embedded in concrete. This method has been proven in the electronics industry for sensitively measuring the effects of very subtle climate changes on the corrosion of integrated circuit lines. The test consists of a very accurate four point resistance measurement of a thin steel or alloy wire embedded in concrete and a similar measurement on an (embedded) reference wire. Any corrosion of the wire will result in mass loss and hence a change in the resistance of the wire. Although fine wire may not seem to have the same surface finish or oxide chemistry as rebar, the wire can be treated to produce appropriate surface chemistry.

Since accurate resistance measurement will be affected by very small temperature fluctuations or instability in the current source, the steel wire resistance is compared to the embedded reference wire, which is either coated or of inert material. Resistance can be measured with a power supply and voltmeter or with an accurate multimeter. By selecting wire size and meter sensitivities, even the loss of a few monolayers of material can be detected.

Our test accurately monitors the corrosiveness of the environment within the concrete over time. Sensors can be placed at various levels in the concrete to observe penetration rates of aggressive species; when threshold levels of critical species such as chloride, sulfate and carbon dioxide are reached, initiation of corrosion can be easily detected by an increase in the resistance. Changes in resistance over time gauge subsequent corrosion rates.

Measurements can also be made at high frequency, which restricts the current to a thin region of the outer surface of the wire. This can be achieved at frequencies of about 1 Mghz and above. Using this "skin effect" makes the technique more sensitive to mass loss in the metal periphery and helps distinguish general corrosion from localized corrosion such as pitting. Our test can also be applied to a segment of the rebar itself, which has the surface oxide (mill scale) of interest.

Since sensors can be embedded in new concrete roads or building structures, our test allows extremely early detection of corrosive conditions so that protective methods can be applied. Our test will therefore save millions of dollars in non-informative testing and infrastructure repairs.

Our test is based on a thorough understanding of corrosion, the chemical and physical attributes of concrete which affect corrosion, the various electrochemical reactions involved, and the electrochemical methods used to quantify corrosion processes. Our test also takes into account the effects of accelerating procedures, admixtures, and alterations produced by age, including those from high temperature or freeze-thaw cycles. The test can also study the effects of cracks, which act as conduits for moisture, air, and chloride penetration. Since cracks dramatically alter the environment in which an inhibitor is meant to operate, they can be produced for testing by a 3-point bending technique and maintained by bracing the specimen. Other permeating factors include the effects of wet/dry cycling or vacuum permeation, elevated temperature (45° C.) versus vacuum desiccator during the drying cycle of wet/dry testing, "wash out" and freeze-thaw conditions.

If the rebar is modeled as a cylindrical rod, the total resistance is equal to $R = \rho l/A$, where $\rho$ is the intrinsic material resistivity, $l$ is the length and $A$ is the cross sectional area of the cylinder. If there is a reduction in $A$, resistance increases. This concept is used routinely for highly sensitive monitoring in real time for the growth of stress corrosion and corrosion fatigue cracks.

The voltage drop that is produced across a low resistivity material is obviously very small, but can be increased by reducing the cross-sectional area, increasing the length, or increasing the current. A four point resistance measurement can detect the loss of 1 micron in diameter in a 12.5 mm diameter bar. The sensitivity of the technique increases to 1 nanometer if a 1 mm diameter rod is used.

If a current source is used with a nanovoltmeter, the current source can be easily stabilized; comparing the voltage drop across the entire bar ($V_T$) to the voltage drop across the end of a bar not in the concrete ($V_e$) allows internal calibration of each sample; the ratio of $V_T/V_E$ will not depend on the magnitude of the current. Heating of the bar will not be a problem and thermal junction voltages, small variations in temperature between the ends of the bar, can be eliminate by reversing the leads and subtracting out the difference between the two measurements.

The advantage of resistance measurement is that the equipment is relatively inexpensive and simple to use, compared to a potentiostat or frequency response analyzer needed for linear polarization and EIS. This invention has the added benefit of allowing large data pools to be acquired for statistical evaluation. This is especially important because most rebar corrosion is a localized phenomenon and will have some statistical variation. Further statistical resolution is obtained when many samples are placed in the same concrete block to produce multiple data points for the same condition. Since the concrete samples are small, many samples can be made and stored in a relatively small space.

Where the corrosion of rebar in a cement matrix is to be investigated, a particularly preferred sensor consists of a fine steel wire (<1 mm dia.) with the same composition as rebar that is also heat treated to produce an equivalent microstructure and oxide chemistry as rebar. The test wire portion of the sensor is electrically contacted to two larger (>3 mm) segments of rebar or a rebar-like material at points which are recessed. The recessed region must be filled with mortar.

The recession of this contact will delay the access of chloride ions to the contact point so that it will not interfere with the material changes being characterized along the central section of the test wire. The larger diameter of the two outside sections of rebar will have a significantly lower resistance than the test wire, and will therefore not interfere with the resistance measurement of the test wire. In addition the natural chemical bond that develops between concrete and bare steel can be established at the points where it exits the concrete. The ends of the larger rebar segments are brought into a protective housing where electrical contacts are established for four-point resistance measurements.

The temperature reference wire is made by embedding a similar small diameter test wire into a glass tube filled with cementitious mortar or cement paste. The wire may or may not have an organic coating. The glass tube is positioned into the recesses of two larger rebar segments as described above. Electrical contact of the small wire is made to the large rebar segments and the recessed areas are filled with cement mortar. The two larger rebar segments are brought through the concrete to the same housing as the test wire leads, and four point electrical contacts are made.

Once constructed, this sensor assembly is held rigidly together by an external brace which connects to the two opposing electrode connector housings. Once the assembly has bene placed into the concrete and the concrete has cured the brace can be removed. The housing has a water-tight cover to protect the electrical connections.

This assembly can be constructed so that multiple test wires are embedded at a certain depth in the concrete or multiple wires at multiple depths can be inserted.

EXAMPLES

Figure 4:
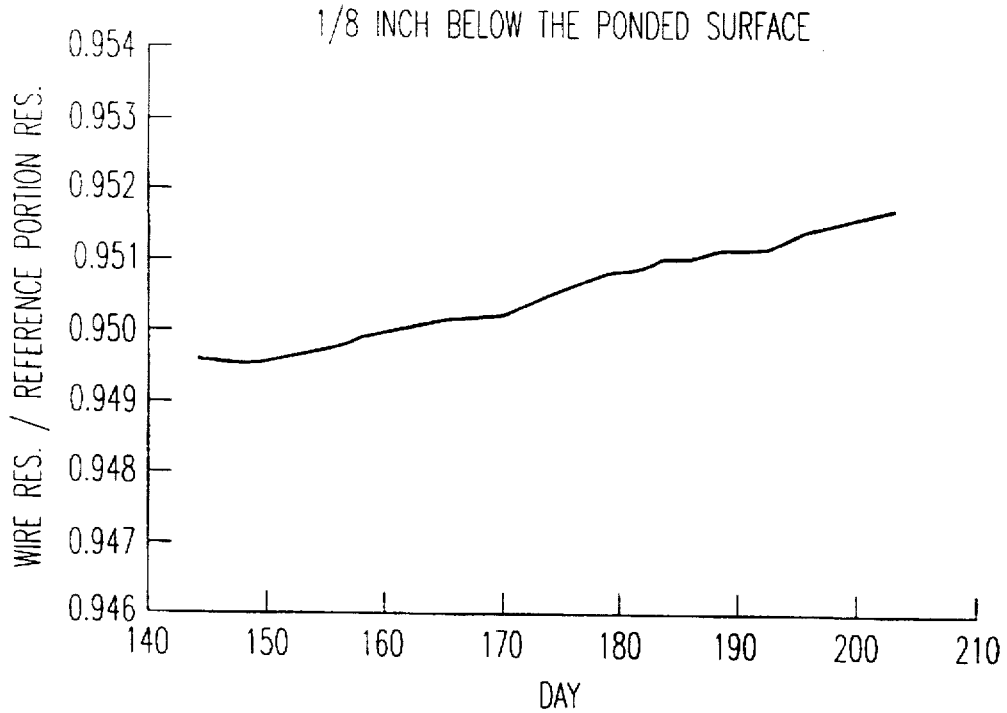
FIG. 4 is a graph illustrating data obtained by using the invention to monitor the corrosion rates in Slag Mortar.

A 9 mil diameter 1040 steel wire was embedded in 50% blast furnace slag mortar ⅛ inch below the top surface. The block was unilaterally ponded with 3.5% aqueous sodium chloride solution from the top surface. Resistance of the wire was periodically measured and compared to the resistance of an embedded reference wire. As shown in FIG. 4, the graph shows a steady corrosion rate in the wire over time.

Figure 5:
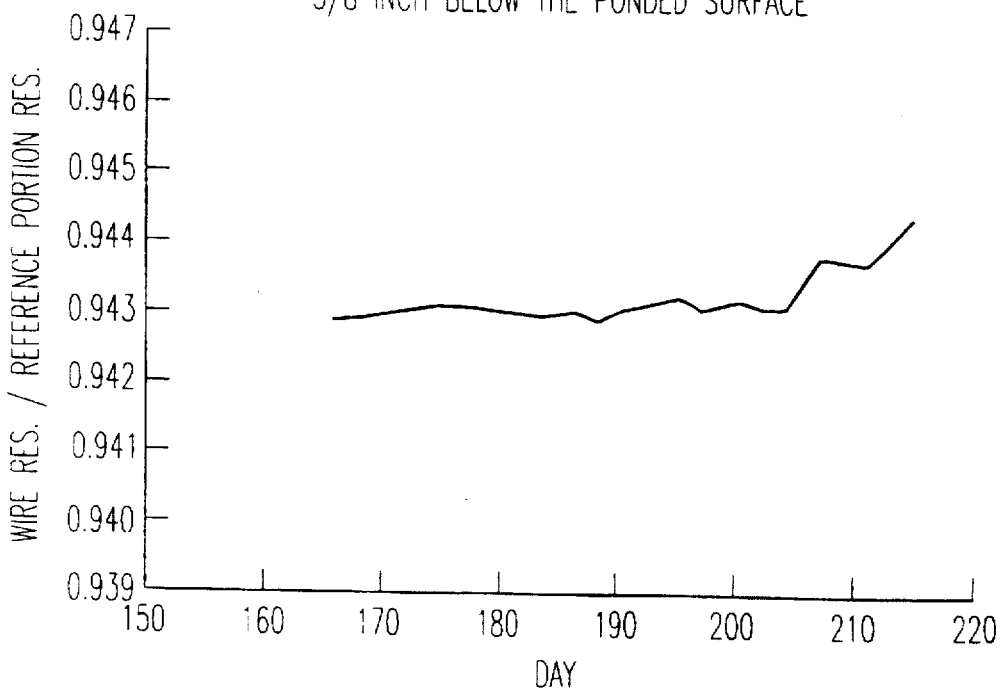
FIG. 5 is a graph illustrating data obtained by using the invention to monitor corrosion in Plain Mortar.

An identical probe was embedded in a block of plain mortar again ponded as above. Resistance of the test wire was measured periodically and compared to the measured resistance of an embedded reference wire. As shown in FIG. 5, initiation of active corrosion occurred between day 190 and 200.

What is claimed is:

1. An in situ sensor to determine the state of corrosion of rebar in a cement matrix, comprising:
   a test wire having a diameter smaller than the rebar embedded in said matrix;
   four electrically conductive leads attached to said test wire for measuring the resistance along a length of said test wire, wherein a portion of said test wire is electrically contacted to a segment of said rebar at points which are recessed and wherein the recessed region is filled with mortar;
   a reference wire embedded in said matrix to which four electrically conductive leads are attached for measuring the resistance along a length of said reference wire, said leads of said test wire and said reference wire being connected to a source of electrical current and a means for determining resistance in said test wire and said reference wire.

2. The sensor of claim 1, wherein said means for determining resistance is a ohmmeter or constant current source and volt meter.

3. The sensor of claim 1, wherein said reference wire is a length of said test wire, wherein said length has been polymerically sealed to isolate it from said matrix.

4. The sensor of claim 1, wherein said test wire and said reference wire are separate wires, and wherein said reference wire is corrosion resistant.

5. The sensor of claim 4, wherein said reference wire is a coated steel wire, a wire comprising gold, or a wire of the same chemistry and microstructure as said embedded test wire, said reference wire being encased within a glass tube filled with said matrix.

6. A reinforced structure of a solid matrix, said structure being reinforced with metal or metal alloy materials, comprising a plurality of the in situ sensors of claim 1 throughout the reinforced matrix portions of said structure.

7. A method of determining the progress of rebar corrosion in a concrete matrix with the sensor of claim 1, wherein said process comprises monitoring the resistance along the length of said test wire of said sensor, as compared with the resistance of said reference wire of said sensor, wherein an increase in resistance along said test wire as opposed to said reference wire is indicative of an increase in corrosion.

8. The in situ sensor of claim 1, wherein said test wire has a diameter no greater than 1 mm.

* * * * *